United States Patent [19]

Shantha

[11] Patent Number: 5,735,817
[45] Date of Patent: Apr. 7, 1998

[54] APPARATUS FOR TRANSSPHENOIDAL STIMULATION OF THE PITUITARY GLAND AND ADJOINING BRAIN STRUCTURES

[76] Inventor: T. R. Shantha, 1657 Kanawha Dr., Stone Mountain, Ga. 30084

[21] Appl. No.: 445,421

[22] Filed: May 19, 1995

[51] Int. Cl.$^6$ .................................................. A61M 29/00
[52] U.S. Cl. ........................ 604/100; 604/113; 604/21; 604/194
[58] Field of Search .................. 604/96, 97–100, 604/113, 43, 21; 606/194; 128/637

[56]         References Cited

U.S. PATENT DOCUMENTS

| 5,304,120 | 4/1994 | Crandell et al. | 604/52 |
| 5,344,398 | 9/1994 | Hara | 604/96 |
| 5,395,331 | 3/1995 | O'Neill et al. | 604/96 |
| 5,398,692 | 3/1995 | Hickey | 128/673 |
| 5,431,648 | 7/1995 | Lev | 606/27 |
| 5,437,637 | 8/1995 | Lieber et al. | 604/96 |
| 5,542,928 | 8/1996 | Evans et al. | 604/113 |
| 5,549,559 | 8/1996 | Eshel | 604/113 |
| 5,549,603 | 8/1996 | Feiring | 604/21 |

*Primary Examiner*—Michael Powell Buiz
*Assistant Examiner*—A. T. Nguyen
*Attorney, Agent, or Firm*—Arthur A. Gardner & Associates, P.C.

[57]         ABSTRACT

A method and apparatus are provided for the stimulation through the sphenoid sinus, the pituitary gland and the adjoining brain structures. The apparatus consists of an inflatable balloon and which is inserted into the sphenoid sinus and inflated. The balloon will stimulate by pressure, heat, cold or electricity, the structures surrounding the sphenoid sinus. The balloon is controlled via connecting tubes and control wires. This method and apparatus has application in the treatment of pain and a number of other maladies of the nervous system.

3 Claims, 2 Drawing Sheets

APPARATUS FOR TRANSSPHENOIDAL STIMULATION OF THE PITUITARY GLAND AND ADJOINING BRAIN STRUCTURES

BACKGROUND OF THE INVENTION

Painful conditions which affect our body are difficult to treat. This is especially true of most cancer pain. The WHO estimates that over 3.5 million people suffer from cancer pain throughout the world. In some types of advanced cancers, the pain cannot be alleviated by any known method. Labor pain in childbirth and surgery affects more than 20 million people annually in the United States. Much pain and suffering is caused by various chronic painful conditions due to central nervous system and peripheral nervous system diseases and dental and musculo-skeletal pain. Many of the pain relieving drugs are expensive and often do not completely alleviate the pain. There are millions of Americans who are partially or totally disabled by pain costing billions of dollars per year. The drugs used to relieve pain have numerous complications, such as bleeding and addiction with prolonged use, thus becoming ineffective. No known specific therapy is effective in alleviating pain.

There are reported cases of cancer pain being treated by removing the pituitary gland or destroying it with an alcohol injection. This is a very drastic procedure done in desperation to relieve pain caused by widespread cancer growth in a patient, It has been resorted to when the pain could not be relieved even with hundreds of milligrams of morphine administration.

An experiment has been reported in which twenty-five patients having advanced cancer had their pain relieved by the insertion of an electrode into the pituitary gland and using electric current to stimulate the gland. This experiment demonstrated that from five to ten minutes of electrical stimulation resulted in from ten hours to ten days of pain relief. There is no satisfactory medical explanation of why the pain was relieved in this experiment. It has been postulated that an endogenous morphine-like substance called endorphins produced by the electrical stimulation, was responsible for the relief. It is interesting, that in the case of this experiment, the pain did not recur in the patients when naloxone, an opiate antagonistic drug, was administered. It has been shown that if pain relief is due to the action of the endorphins and the opiates, the pain will recur with the administration of naloxone. This clearly indicates that other mechanisms of pain relief were involved in this experiment. Unfortunately, this method is very invasive, expensive, fraught with complications such as meningitis, cerebrospinal fluid leakage and even death. That is why this procedure has not been clinically used except in this experimental study.

It is clear, from the above experimantal study, that the direct electrical stimulation of the pituitary gland, alcohol injection and removal of the pituitary gland will result in the reduction of pain. It may be that the hypothalamus and the thalamus are also involved in the pain relief obtained by these methods. The hypothalamus is located above and connected to the pituitary gland. The hypothalamus is connected to the brain stem and thalamus which have descending pain inhibitory nerve tracks. It appears that these methods may act by a mechanism, through production of other neurotransmitters, and does not involve the endorphin or opiate receptors.

Support of a theory that mechanisms not involving the endorphin or opiate receptors are at work and has been found upon the autopsy of the patients where alcohol was injected into the pituitary gland. In these cases, the pituitary gland was not totally destroyed and, in fact, the pituitary gland was intact in many of these patients. However, all of these patients got some relief. These autopsies demonstrate that the removal or destruction of the gland is not needed to obtain pain relief. These autopsies demonstrates that the removal or destruction of the gland is not needed to obtain pain relief. Stimulation of the pituitary gland by alcohol injection or electrical stimulation has been shown to relieve pain.

The pituitary gland is surrounded by and connected to the hypothalamus, thalamus, central gray, reticular system, hippocampus, parahippocampal cingulayte gyrus. The basal ganglion, red nucleus and substantia nigra are in close proximity to the hypothalamus and are inter-linked Electrical impulses imparted to the pituitary gland may spread to the above brain structures, and play an important role in alleviating pain and other diseases. The pituitary gland rests immediately above the thin sphenoid bone which will allow the electrical impulses to be transmitted to the surrounding, above-described brain structures.

Sella turcica of the sphenoid bone lodging the pituitary gland is walled by sphenoid sinus, and is surrounded by olfactory, optic, oculomotor, abducent, trochlear, and trigeminal nerves, as well as the spheno-palatine and otic ganglion. These nerves are separated from the sphenoid sinus by a thin wall.

In recent years a number of devices have developed for insertion into the human body to treat a particular problem, including the dilation of coronary blood vessels and stimulation of the heart and spinal cord. The miniaturization of various devices has made this possible. For example, blockage of the heart arteries by fatty deposits can be eliminated or reduced in many cases by angioplasty. In angioplasty, an inflatable ball attached to a catheter, is inserted into the artery and directed to the point of blockage. The balloon can then be inflated and moved to eliminate the blockage.

SUMMARY OF THE INVENTION

It is an object of the present invention to develop a device to alleviate pain in patients.

It is a further object of this invention to develop a device for stimulating the surface of the sphenoid sinus, especially its roof and lateral walls, where the pituitary gland and a number of neurological structures are located.

It is a further object of this invention to develop a device for stimulating the surface of the sphenoid sinus which the patient can use while engaging in normal activities and being ambulatory.

Applicant has developed a device for stimulating the interior surface of the sphenoid sinus, its wall and surrounding structure. Applicant's apparatus consists of an insertion body, having a flexible outer surface and adapted for insertion into the sphenoid sinus. The insertion body is constructed of a flexible material which contracts and conforms to the interior surface of the sphenoid sinus. Basically, the insertion body is an inflatable outer membrane or balloon. This balloon is attached to a flexible robing through which air or fluid can be pumped to inflate the balloon to position the balloon against the surface of the sphenoid sinus. Fluid can be circulated into the balloon by means of a robe, part of which is also part of the insertion body. This fluid may be heated to from 42°–44° C. or higher, if so desired, to stimulate or decrease the output of pituitary hormones, including growth hormone from the pituitary gland. Other means, such as a device embodying the Peltier effect, can be used to heat the outer surface of the balloon. Heating will enhance the conduction of electrical impulses, facilitate the stimulation of pituitary gland and other surrounding nerve structures.

The inflatable balloon is inserted in the uninflated state into the hollow sphenoid sinus through the sphenoid foramina which connects to the nose. The balloon is then inflated with liquid or air under slight pressure.

In some cases it may be desirable to cool the liquid depending on the purpose for which the device is being used (e.g., to lower the activity of the hyperactive pituitary gland).

Electrical stimulators can be placed along the outer surface of the inflatable balloon for stimulating the pituitary gland and other nerve structures surrounding the sphenoid sinus. Temperature sensors can be placed on the outer surface of the balloon to determine the temperature which will approximate the temperature of the surface of the sphenoid sinus. The interior shape of the balloon can be examined by using a fiber optic connection. By visual inspection through the fiber optic connection, the approximate size and shape of the sphenoid sinus can be determined and whether the balloon is filling that space or not.

Means can be provided for the quick detachment of the balloon from the rest of the apparatus. Under those circumstances, the balloon can be left in the sphenoid sinus cavity and its activities controlled by a controller, outside the body, through radio transmission, to a receiver located in the balloon. The battery powered receiver can then direct that current be provided to electrical stimulators on the outside of the balloon or to heating elements inside the balloon to heat the fluid to a desired temperature. This device will allow full mobility by the patient while the sphenoid sinus is being stimulated.

The apparatus and method of this invention is useful in the treatment of acute and chronic pain of headaches. It can also stimulate the structures surrounding the sphenoid sinus, and particularly the pituitary gland, which may be useful in treating various diseases that arise from the central and peripheral systems. A fluid can be heated or cooled and pumped into the balloon to enhance the output or decrease the output of pituitary growth hormone from the pituitary gland.

Thermocouples can be applied at the tip of the catheter inside the balloon. They are connected to the N-doped and P-doped legs of the semiconductor material which when connected to the direct current can heat or cool the thermocouples depending on the direction of current flow. This heating and cooling is called Peltier effect and was discovered in 1831 by a Swiss Scientist. The same principle is used in the heat pump. Devices embodying the Peltier effect are currently being used to cool and heat the tissue and fluids in the body. Instead of using the heating or cooling circulating pump to heat or cool the fluid omission inside the inflated balloon as desired to treat various conditions and to increase or decrease the pituitary function. In some applications, it may be desired to simply use the inflated balloon with its pressure stimulating the sphenoid sinus.

A catheter can be attached to the balloon through which drugs may be infused into the sphenoid sinus for absorption by the central nervous system directly across the sphenoid bone.

This device may have application in the treatment of many other diseases such as epileptic attacks, chronic fatigue syndrome, senility with hypopituitary and hyperpituitary function, dental pain, various kinds of headaches, Parkinson's disease, multiple sclerosis, thalamic pain, Alzheimer's disease, spastic paraplegia, cerebral palsy and downs syndrome because of its ability to be inserted into the sphenoid sinus and its actions controlled.

DETAILED DESCRIPTION OF THE DRAWINGS

A. Anatomy

The sphenoid sinus is located within the body of the sphenoid bone, posterior to the upper point of the nasal cavity. The sphenoid sinus consists of two large irregular cavities separated by a bony septum. The middle of the anterior wall of the sphenoid bone forms a crest, which articulates with the perpendicular plate of the ethmoid bone, which forms the nasal septum. On each side of the sphenoid crest, a rounded opening, called the sphenoid foramina, about 4 mm in diameter, opens into the sphenoid sinus. The sphenoid sinus is 2 cm high, 2 cm wide and 2.1 cm anteroposteriorly. The sphenoid communicates with the sphenoid-ethmoidal recess in the upper part of the nose through this aperture. It is supplied by the posterior ethmoidal blood vessels. Lymph is drained by retropharyngial lymph nodes. It is innervated by the posterior ethhmoidal nerve and orbidal branch of the sphenopalatine ganglion. It is related to pituitary gland and hypothalamus. On each side of the sinus is the cavernous sinus containing carotid arteries and the first five cranial nerves.

B. Description of the Drawings

Figure 1:
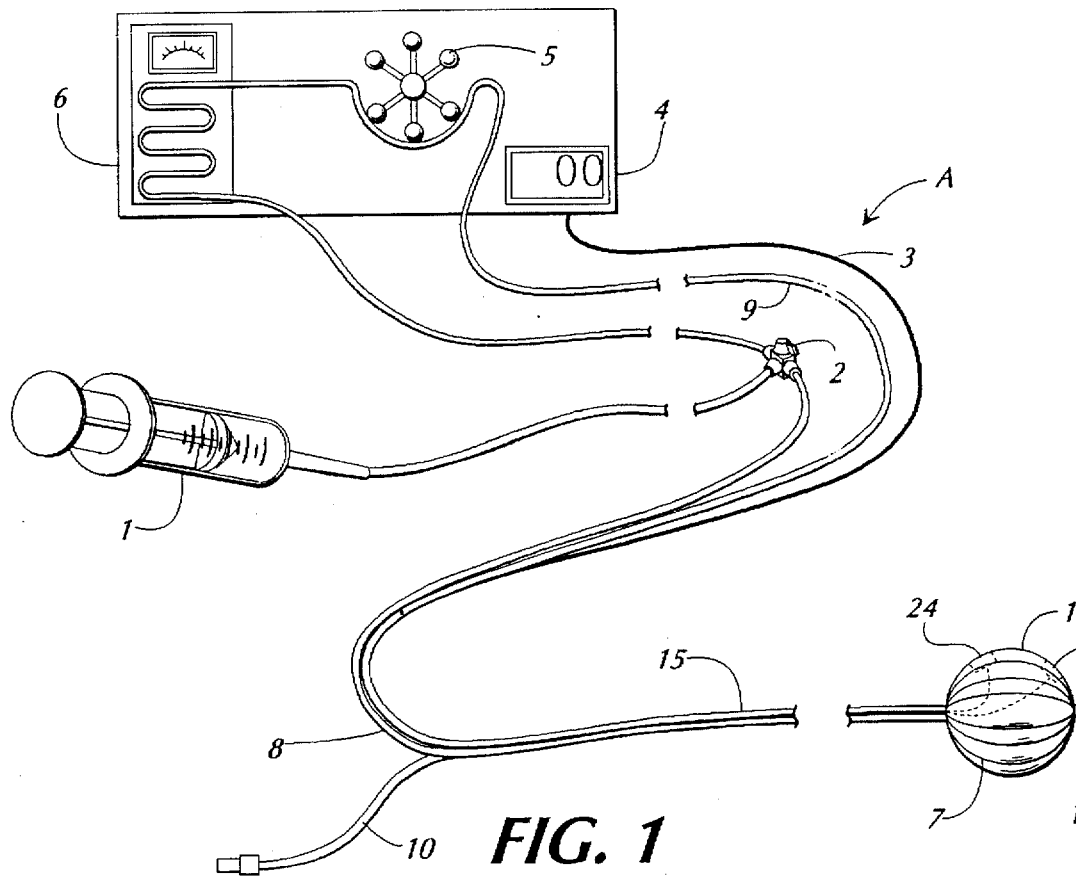
FIG. 1 is a schematic illustration of the preferred embodiment of this invention for the localized stimulation of the structures surrounding the sphenoid sinus cavity such as the pituitary gland, brain, and the cranial nerves which surround it. It has a temperature sensor, heating and cooling system and electrical stimulator.
Figure 2:
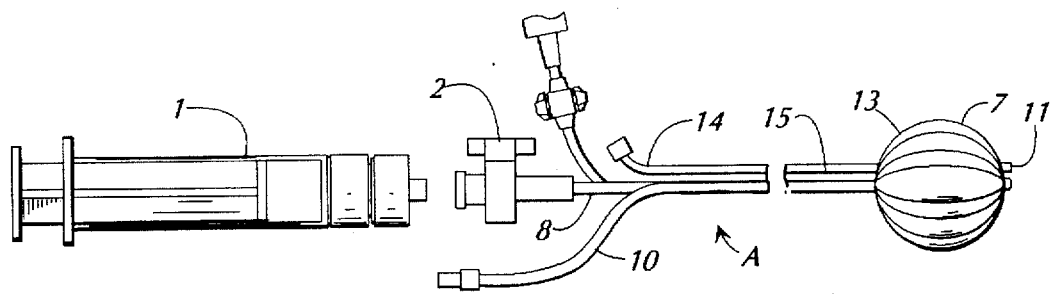
FIG. 2 is a schematic illustration of the apparatus of this invention which has a separate infusion tube for the transmission of the fluid into the sphenoid sinus, balloon inflator, fiberoptic to visualize the passage of the device and an electrical stimulator.
Figure 3:
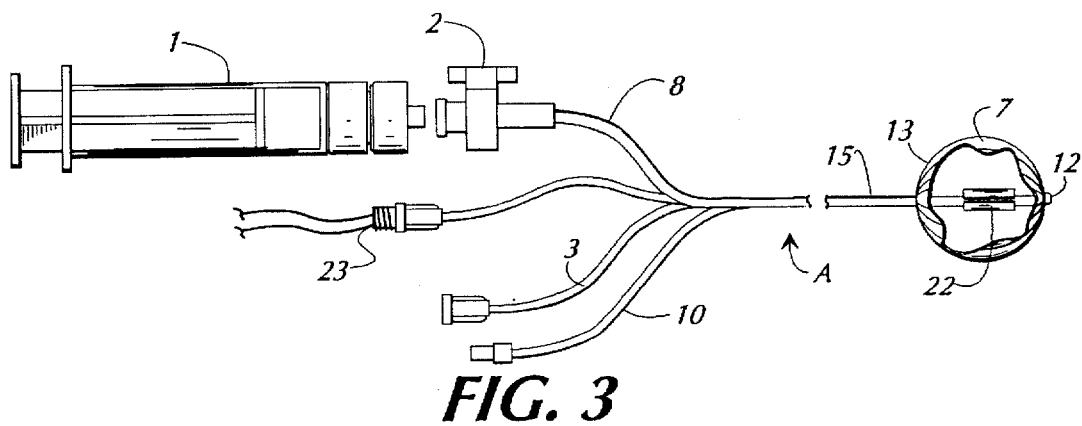
FIG. 3 is a schematic illustration of the apparatus of this invention which has a separate infusion tube for the transmission of the fluid, wires connected which can be connected which can be connected to direct electrical current to heat or cool the fluid surrounding the balloon using the Peltier effect as shown in the insert. It has a temperature sensor, electrical stimulator, and fiberoptic.
Figure 4:
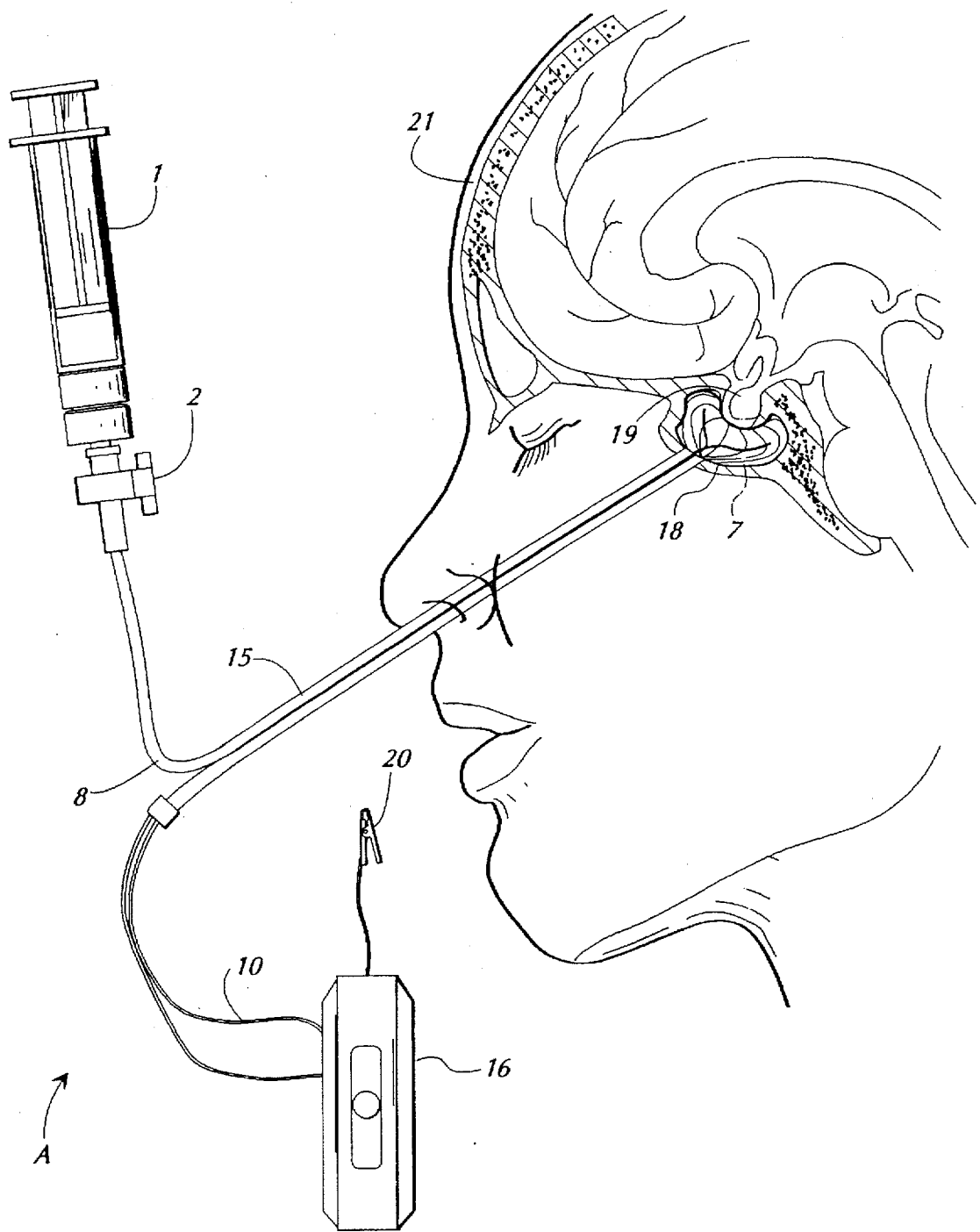
FIG. 4 is a schematic illustration of the preferred embodiment of this invention with the apparatus in place in the human head with the balloon in the sphenoid sinus cavity with the electrical stimulator.

The apparatus A for stimulating the sphenoid sinus of this invention, as illustrated in FIG. 1, consists of two parts. One part is the insertion body, which is inserted through the nose in the human head 21 through the sphenoid foramina and then into the hollow sphenoid sinus 18 with the aid of fiberoptic scope. The insertion body consists of two parts. One part is an inflatable outer membrane or balloon 7 which is adapted in size and flexibility to fit inside the sphenoid sinus cavity 18, as illustrated in FIG. 4. The interior of this balloon 7 is connected to an inflation tube 8 which in turn is connected through an inflation stopcock 2 and a tube to the inflation syringe 1. The inflation syringe 1 can be used to pump air or fluid through the inflation tube 8 to the interior of the balloon, so it inflates, filling the sphenoid sinus cavity 18 during the operation of the apparatus. An infusion tube 9 may also be connected to the interior of the balloon 7 and connected to an infusion pump 5. The infusion pump 5 can be used to pump fluid at ambient, elevated or low temperatures through the infusion tube 9 and to the interior of the balloon 7 during the operation of the apparatus. A device 6 for heating or cooling the fluid to be pumped into the interior of the balloon 7 can also be included in the apparatus.

For some types of treatment, the stimulation of the sphenoid sinus can be enhanced by vibrating the balloon. This can be accomplished by generating pulses through the inflation tube 8 or infusion tube 9.

The status of the interior of the balloon 7 can be visually examined through a fiber optic connection 14 if desired. The operator can determine whether the balloon 7 is fully inflated and its configuration through the fiber optic connection 14. Photographs can be taken through the fiber optic connection 14 for future study.

The balloon 7 can be provided with multiple electrical leads 13 on the exterior of the balloon 7. These leads can be connected by electrical connectors 10 to an electrical output device 16, as illustrated in FIG. 4. This electrical output device 16 can be connected to a source of electricity by a clip 20. Electrical stimulus can be provided to the electrical leads to stimulate the pituitary gland, pituitary hypophysal track and surrounding nerve structures by stimulating the interior surface of the sphenoid sinus cavity and its walls, which will in turn transmit electrical impulses to the above-mentioned structures, for certain types of treatment of treatment of diseases of the nervous system and pain.

A catheter 11 can be placed on the balloon surface with a suitable robe to administer drugs or other fluids directly to the sphenoid sinus cavity 18, as desired for treatment. The drugs can be infused so that they will be absorbed by the central nervous system directly across the sphenoid bone. In this way a small dosage of drugs can be used instead of using large dosages systematically. The antibiotics and anticoagulants may be impregnated into the surface of the balloon, for transmission to the surface of the sphenoid sinus cavity, to prevent clotting and infection.

All of the tubes and connectors to the balloon 7 can be assembled together in a connector assembly 15. The inner portion of this connector assembly 15 constitutes part of the insertion body. This assembly needs to be small in diameter and flexible for easy insertion through the nose and into the sphenoid sinus cavity.

A temperature sensor wire 3 can be connected to a temperature sensor 24 and indicator 4. The temperature sensor wire 3 can be connected to sensors 24 in the balloon 7 to determine the temperature of the balloon surface and the structures in the immediate vicinity of it. A control panel 17 can be used for controlling the operation of this apparatus A for stimulating through the sphenoid sinus.

C. Theories of Pain

Even today, it is not known exactly how pain is perceived. The latest Melzack and Wall's Gate theory explains that the pain is perceived by the brain when the injury (pain) impulses are allowed to be transmitted at the spinal cord level gate. Pain is not perceived when the gate is closed due to any number of reasons. Though this theory does not fulfill all the necessary details, it does give a reasonable scientific explanation. If the gate at the spinal cord level is involved in transmitting pain, why is the cancer pain relieved by removal and stimulation of pituitary gland? It may be there is more than the gate involved. Generating electrical impulses in the balloon results in electrical stimulation of the pituitary gland which spreads to the surrounding hypothalamus and the eipthalamus, thalamus centers and brain stem and thereby prevents the spread of painful stimuli by acting as counter current and thus, prevent them reaching the higher brain centers where they are perceived as pain. These stimulations can modify the entire nervous system's perception of pain. It may be useful also in treating other diseases or their symptoms.

Recently, there has been abundant evidence to support the fact that peripheral pain stimulus (nociception) entering the spinal cord through A-delta and c-fibers can last up to 20 seconds, which is about 2000 times longer than most synaptic potentials evoked by A-Beta fibers. This is to say that a few seconds of c-fiber input results in several minutes of postsynaptic depolarization. This cumulative activity of depolarizing results from activation by glutamate of N-melthy D-aspartic acid (NMDA) receptors. Thus, the continued peripheral nociceptor afferent input to the spinal cord results in sensitization of spinal cord and central neurons. This phenomenon is called central sensitization. This central sensitization is truly pathologic because pain is evoked by A-Beta low threshold mechanoreptors nerve fibers which normally do not produce painful sensation. Pain results from changes in sensory processing in the central nervous system (spinal cord and brain). This central sensitization can be prevented by blocking the nociceptive impulses before they sensitize central neurons by regional anesthesia and pain relieving medications before the injury by anesthesia and pain relieving medications before the injury (surgery, trauma). It is called preemptive analgesia. Physiological pain differs from pathological pain by the presence of pathologic hypersensitivity. The apparatus of this invention may reverse the central sensitization phenomenon. It can act as a preemptive analgesia. This apparatus, with the electrical leads attached to the balloon, can generate a stream of impulses which descend down and counteract and desensitize nerves, thereby establishing physiological balance in the central neurons and prevent pain impulses from reaching the higher centers in the brain.

D. Medical Applications of the Apparatus

The use of the apparatus of this invention is most important in blocking pain due to any cause, including trauma, giving birth to a baby, after surgery, cancer pain, pain of back injury, fibromyalgia, reflex sympathetic dystrophy, arthritic pain, pain due to neuropathies, phantom pains and chronic pains of many kinds. Most of the diseases in the body are signaled through the development of pain. By using this invention, this method can be used as an adjuvant to anesthesia. It may be used for the treatment of many diseases where stimulation, whether by pressure of the balloon, electrical stimulation, elevated or cool temperatures, of the sphenoid sinus and surrounding neurological structures are useful in treating a disease. Among the diseases where it may have an application include epilepsy, multiple sclerosis, chorea (Huntington's disease), downs syndrome, Parkinson's disease, dementia, (including Alzheimer's disease), obesity, sleep disorders, senility, depression, drug withdrawal or addiction and chronic fatigue syndrome.

The apparatus of this invention may be useful in treating a number of diseases because of its ability to stimulate the pituitary gland and surrounding neurological and brain structures through the sphenoid sinus. The ability to precisely control this device and provide the precise amount and type of stimulation within a wide range makes its application ideal for treating a number of maladies. Because the stimulation is directed at a specific area, it does not have side effects that affect other parts of the body as in the case of systemic drugs. The apparatus of this invention provides an additional tool for the specialized physician for treating a number of maladies.

E. Method of Operation

In operation, the balloon 7 of the apparatus A for stimulating the sphenoid sinus is deflated and inserted through the nose into the sphenoid foramina which opens into the nose and then into the cavity of the sphenoid sinus 18. If needed, a fiber optic scope can be used to facilitate its introduction. After insertion of the balloon 7 into the sphenoid sinus 18, the balloon can be inflated by the inflation syringe 1 pushing fluid (i.e., air or liquid) through the inflation tube 8 and into the interior of the balloon. For some applications, the electrical stimulation of the balloon transmits electrical impulses through the surfaces of the sphenoid cavity into the surrounding structures, which will achieve the desired therapeutic effect. For some applications simple pressure may be applied on the walls of the sphenoid sinus to prevent bleeding or cerebro-spinal fluid leakage.

If it is desired to apply heat to the surface of the sphenoid sinus cavity 18, the liquid can be heated by the heating device 6 and pumped by the infusion pump 5 through the infusion tube 9 into the interior of the balloon. A return tube (not shown) can be provided if continuous circulation of a fluid is desired. The fluid can be heated and circulated in the balloon at a temperature of 42°–44° C. and in some cases at higher temperatures. In some applications, it may be desirable to cool the liquid being used to fill the balloon. Theremocouples 25 can be used at the tip of the catheter, inside the balloon 7 to heat or cool the fluid in the balloon using direct current (Peltier effect).

A temperature indicator 4 can be used to determine the temperature on the surface of the balloon. The temperature indicator 4 is connected by a temperature sensor wire 3 to the temperature sensors 24 on the surface of the balloon 7. In this way, the temperature on the surface of the balloon can be monitored to determine that it is within the desired range.

In some cases, electrical stimulation of the exterior surface of the sphenoid sinus cavity 18 may be desired. Under these circumstances, electrical leads 13 can be placed on the outside surface of the balloon 7 and connected by an electrical connector or wire 10 to an electrical output device 16 which in turn is connected by a clip 20 to a power source (not shown).

The mount of electrical current used for stimulation or the temperature of the fluid in the balloon can be controlled by a control panel 17 order to keep the procedure within the desired parameters.

The only part of the apparatus A that is inserted into the human head is the balloon 7 and part of the connector assembly 15. The balloon can be withdrawn from the sphenoid sinus cavity 18 when the air or the fluid is withdrawn from the balloon by the inflation syringe 1. If fluid has been inserted into the balloon, it can be withdrawn by reversing the infusion pump to pump the fluid out of the balloon. When the balloon is in the deflated state, it can easily be withdrawn from the sphenoid sinus cavity 18.

This device is inserted with the patient lying down with the neck extended with a small support under the patient's shoulders. The nose is sprayed with a local anesthetic and neosynephrine or afrin, to shrink the mucus membranes. Pledget soaked in local anesthetics and vasoconstrictors can also be packed with angled forceps. Antiseptic solutions are also applied. As the local anesthetic takes affect, a fiberoptic nasoscope is passed all the way up to the spheno-ethmoidal recesses located at the posterior upper angle of the nose. Then the body of the apparatus is guided gently into the sphenoid sinus through the sphenoid foramina. If the opening of the sphenoid sinus is narrow, it can be enlarged by dilators or inflatable balloons or bougie. The balloon can be inflated with a liquid and the stimulation started. It may be necessary in some cases to insert the apparatus into both right and left sphenoid sinus to achieve the desired therapeutic scale.

In another embodiment the balloon can be equipped with a miniature battery, receiver and controller (not shown). The balloon can be inserted into the sphenoid sinus cavity 18 with the connector assembly 15 being detached after the proper operating conditions in the balloon have been obtained. A radio transmitter, which is carried by the patient, can be used to transmit messages to the receiver in the balloon for either applying electrical current from the battery to the electrical leads 13 or for heating the interior of the balloon 7 with an electrical resister element (not shown). Under these circumstances, the patient can be ambulatory and engage in regular activities. The balloon 7 can be removed by using an instrument to puncture the balloon releasing the fluid or air inside and then removing it in the same manner in which it was initially inserted.

While the present invention has been described with reference to the preferred embodiment, it shall be understood by those skilled in the art that various changes may be made and equivalents may be substituted for elements thereof without departing from the scope of the invention.

Therefore, it is intended that the present invention shall include embodiments failing within the scope of the appended claims.

I claim:

1. An apparatus for stimulating the sphenoid sinus and proximate structures of the human body, the apparatus comprising:

an insertion body having a balloon with a flexible outer surface adapted to contact and conform to the interior surface of the sphenoid sinus, the balloon having an interior;

means connected to the interior of the balloon for inflating the balloon while in the sphenoid sinus;

a thermocouple connected to and residing within the interior of the balloon for locally heating and cooling fluid present within the balloon and for locally heating and cooling the interior surface of the sphenoid sinus immediately adjacent the outer surface of the balloon;

a temperature sensor connected to the interior of the balloon and connected to a temperature indicator external to the balloon for monitoring the temperature of the outer surface of the balloon;

electrical stimulators attached to the outer surface of the balloon;

connection means for connecting the electrical stimulators to a power source and control device outside of the sphenoid sinus for stimulating the sphenoid sinus and proximate structures with controlled electric current; and, means attached to the outer surface of the balloon for discharging drugs from the insertion body into the interior of the sphenoid sinus for absorption by the pituitary gland or central nervous system.

2. The apparatus of claim 1 which a tube is connected to the balloon for infusing fluid into the interior of the balloon and the apparatus further comprises a device external to the balloon and connected to the balloon for heating and cooling fluid prior to infusion into the interior of the balloon while the balloon is in the sphenoid sinus.

3. The apparatus of claim 2 in which the means for inflating the balloon is at least one tube which is connected to an inflator.

* * * * *